United States Patent [19]

Kenning

[11] Patent Number: 5,717,602
[45] Date of Patent: Feb. 10, 1998

[54] AUTOMATED ELECTROPHORESIS AND ANALYSIS SYSTEM

[76] Inventor: Gregory G. Kenning, P.O. Box 626, Crestline, Calif. 92325

[21] Appl. No.: 675,066

[22] Filed: Jul. 3, 1996

[51] Int. Cl.⁶ ........................................... C25B 15/02
[52] U.S. Cl. ........................................ 364/500; 204/457
[58] Field of Search ................................. 364/500, 550, 364/496, 497, 498, 499, 571.01, 571.02; 204/450, 456, 457, 461, 554, 600, 606, 607, 612

[56] References Cited

U.S. PATENT DOCUMENTS

| | | |
|---|---|---|
| 4,335,427 | 6/1982 | Hunt et al. . |
| 4,389,677 | 6/1983 | Rushby et al. . |
| 4,810,348 | 3/1989 | Sarrine et al. . |
| 4,811,218 | 3/1989 | Hunkapiller et al. . |
| 4,841,443 | 6/1989 | Kakumoto et al. . |
| 4,870,692 | 9/1989 | Zuiderveld et al. . |
| 4,874,492 | 10/1989 | Mackay . |
| 4,890,247 | 12/1989 | Sarrine et al. . |
| 4,958,281 | 9/1990 | Hara . |
| 4,971,677 | 11/1990 | Kambara et al. . |
| 4,980,827 | 12/1990 | Hara . |
| 5,062,942 | 11/1991 | Kambara et al. . |
| 5,068,909 | 11/1991 | Rutherford et al. . |
| 5,073,963 | 12/1991 | Sammons et al. . |
| 5,104,512 | 4/1992 | Gombocz et al. . |
| 5,121,320 | 6/1992 | Aoki et al. . |
| 5,147,522 | 9/1992 | Sarrine . |
| 5,162,654 | 11/1992 | Kostichka et al. . |
| 5,192,412 | 3/1993 | Kambara et al. . |
| 5,290,419 | 3/1994 | Kambara et al. . |
| 5,294,323 | 3/1994 | Togusari et al. . |
| 5,410,412 | 4/1995 | Gombocz et al. . |
| 5,419,825 | 5/1995 | Fujii . |
| 5,460,709 | 10/1995 | Sarrine et al. . |

*Primary Examiner*—Emanuel T. Voeltz
*Assistant Examiner*—M. Kemper
*Attorney, Agent, or Firm*—Knobbe, Martens, Olson & Bear, LLP.

[57] ABSTRACT

An automated electrophoresis apparatus defining an enclosure that receive a sample gel containing sample material. A voltage is applied to the sample gel and the material migrates through the sample gel. A CCD camera is used to periodically obtain digital images of the sample gel wherein bands of migrated sample material appear in the images. The apparatus includes a computer that determines the location of starting wells in the sample gel that contain sample material and the computer uses this information to define regions of the sample gel where electrophoretic migration will occur. The computer then obtains an integrated intensity value of each of the rows within the region which provides an indication of the location and intensity of the bands of migrated sample material.

17 Claims, 7 Drawing Sheets

AUTOMATED ELECTROPHORESIS AND ANALYSIS SYSTEM

BACKGROUND OF THE INVENTION

This application claims the benefit of U.S. provisional application Ser. No. 60/011,163, filed on Feb. 5, 1996.

1. Field of the Invention

The present invention relates to a system for obtaining electrophoresis data and analyzing the data and, more particularly, concerns an automated system for automatically acquiring electrophoresis data over time and providing an analysis of the data.

2. Description of the Related Art

It has long been known that different sized charged molecules will diffuse through material, in response to an applied voltage, at different rates. This process is generally known as electrophoresis and electrophoresis is commonly used for such things as genetic typing and the like. In one common type of electrophoresis, known as a slab-gel electrophoresis method, a gel and gel holder are set in a buffer material and the samples of molecules are positioned in one or more starting wells in the gel. A voltage is then applied to the gel and the molecules are induced to diffuse through the gel in a direction dictated by the field resulting from the applied voltages.

Typically, a fluorescent dye is added that is attracted to the molecules and the gel is exposed to ultraviolet light which causes the molecules to fluoresce which thereby allows for separation and identification of the molecules based upon their relative positions in the gel. It will be understood that smaller molecules are likely to migrate farther in the gel as compared to larger molecules in response to the applied voltage. Typically, the gel is exposed to the florescent light after a set period of time and a photograph or other image is then acquired to record the data.

Based upon the relative positions of the molecules within the sample, the presence or absence of certain molecules can be determined. This allows for use of electrophoresis for such things as genetic typing and forensic analysis. In these applications, a bio-molecule is basically replicated multiple times using well-known techniques and is then deposited in one or more starting wells in the electrophoresis gel. A voltage is then applied to the gel and the bio-molecules then migrate and diffuse through the gel in response to the applied voltage. After a period of time, the bio-molecules will have separated into different bands in the gel. In particular, bio-molecules of different size reach different locations within the gel thereby separating the genetic material into bands. It will be appreciated, for example, that the presence or absence of certain bio-molecules can be determined using electrophoresis analysis by comparing the unknown electrophoresis sample to a known electrophoresis sample in determining whether certain DNA molecules are present.

One difficulty with the typical electrophoresis apparatuses and methods that are currently used is that they are often cumbersome and time consuming. Specifically, with the typical electrophoresis apparatus the operator has to prepare the gel, position the molecules within the wells in the gel, and then position the gel within an electrophoresis box. When the gel is in the electrophoresis box, the voltage is then applied to the gel and the operator typically has to manually time the application of the voltage until a desired time has gone by and then expose the gel to the florescent light and capture an image of the gel. Often, the captured image is photographic which then requires that the operator have the film developed. It will be appreciated that this is a very time consuming and inefficient activity for the operator. Further, once a sample is positioned within the electrophoresis box, the operator typically has to wait until the electrophoresis analysis on that particular sample has been completed prior to starting another sample.

Hence, the typical electrophoresis apparatus used for PCR type applications typically requires an individual who is highly trained to spend an inordinate amount of time performing relatively simple tasks. Consequently, there is a need for a more automated electrophoresis apparatus and method that automates a significant portion of the electrophoresis process and thereby allows the operator to concentrate on the analysis of the data.

For example, in the prior art electrophoresis systems, the operator must generally designate the portions of the Agar gel used in Polymerized Chain Reaction (PCR) type electrophoresis that contains the sample material. This often requires the operator to place a template onto the gel prior to obtaining any pictures. It will be appreciated that this can be time consuming and tedious. Even if an automated system is being used, the template must generally be positioned over the gel and the regions of the template that contain the sample must be designated for the automated system.

Another difficulty with prior art automated electrophoresis apparatuses is that there is inherent inaccuracy in how digital images of the sample are processed. For example, prior art electrophoresis system that obtain digitized images generally assign a background value for each pixel. This value is subtracted from each of the pixels in the image so that objects in the image of the sample that are part of the background are subtracted out of the image. However, the background value is usually obtained by selected a portion of the region of the gel not containing any sample material and determining an average pixel intensity. This average pixel intensity then becomes the background value and is subtracted from each of the pixels of the image throughout the entire image. It will be appreciated that this form of background subtraction can introduce errors as it is based on the assumption that the background of the entire image is the same as the background in the region sampled.

Hence, from the foregoing, there is a need for an automated electrophoresis apparatus that is capable of automatically capturing electrophoresis data without requiring the operator to spend significant amounts of time performing tedious tasks. To this end, there is a need for an electrophoresis apparatus that is capable of determining the location of wells in a sample that contains the sample material so that the region of the sample that is to be evaluated in subsequent images can be defined and analyzed. Further, there is a need for an electrophoresis apparatus that is capable of automatically performing accurate digital calculations such as background subtraction and integrated intensity lending to an apparatus that can obtain quantified data.

SUMMARY OF THE INVENTION

The aforementioned needs are satisfied by the electrophoresis apparatus of the present invention which is comprised of an electrophoresis enclosure which contains the sample with the sample material positioned therein, an electronic image capture device which captures images of the sample in the enclosure, a lighting system which illuminates the sample in the enclosure, an electronic storage system which stores data captured by the image capture device and a control system which controls the voltage applied to the sample, the image capture device, the lighting system and the electronic storage system.

In the preferred embodiment, the sample comprises an Agar-type gel with one or more starting wells having the sample material positioned in the starting wells. The gel is positioned on a platform within an enclosure. The lighting system includes one or more ultraviolet lights that are positioned so as to illuminate the sample in the enclosure. The image capture device is positioned over the platform that contains the sample. A control system is configured so that it induces a voltage to be applied to the electrophoresis platform to initiate the electrophoresis process in the sample gel and then, at periodic intervals, induces the lights to illuminate the sample and induce the electronic image capture device to capture an image of the sample. In the preferred embodiment, the image capture device is a charge couple device (CCD) camera. The CCD camera obtains a digital image of the sample which is then stored in the electronic storage system. In the preferred embodiment, the electronic storage system and the control system is implemented using a personal computer with appropriate custom software.

The custom software in the personal computer initially implements a run-time program wherein the image capture device captures a background picture of the sample and then subsequently a voltage is applied to the sample and the image capture system periodically captures images of the electrophoresis sample. The background images are subtracted from the subsequently taken images of the sample pixel by pixel to thereby reduce possible sources of error in the subsequent analysis of the electrophoresis data. The computer directs the image capture system and the lights to periodically take images of the sample during the electrophoresis process until a preselected number of images are captured. In one implementation, additional samples can be added to the electrophoresis enclosure while the system is capturing data from previously positioned samples.

In another aspect of the present invention, the system automatically determines the regions of the gel that contain molecular material. In the preferred embodiment, a gel substrate is initially perforated with starting wells and molecular material is then positioned within the starting well. The molecular material includes a loading buffer and the background image generally displays the gel with one or more starting wells loaded with the loading buffer. The loading buffer then migrates out of the starting well upon initiation of the electrophoresis process in the gel. An image is taken shortly after the initiation of the process and the loading buffer then appears as a band that has migrated out of the starting well.

By performing a pixel by pixel subtraction of the background image from the first image taken, and by inverting the result, the starting well will appear in the resulting image as a dark bands corresponding to the starting wells. The computer is preferably configured to perform a row by row intensity integration over the entire sample to determine the location of the dark band. Once the band is located, a well is then defined which where subsequent electrophoretic migration will occur. Hence, for subsequent determination of the location and intensity of bands, the computer only has to perform the processing on pixels that are located within the pre-defined well.

The location and intensity of the fluorescent bands can then be calculated and integrated by the computer. The location can be used to determine the presence of particular molecules. Further, the integrated intensity value provides an indication as to the quantity of molecules that are contained within a particular band. This quantitative data of the number of molecules that have diffused through the sample to form a particular well can then be used for quantitative analysis and comparison.

Another aspect of the preferred embodiment is that an automatic buffer fluid pumping system is included. During the electrophoresis process, the gel is generally submerged in a buffer fluid. In the preferred embodiment, the control system controls a heating system and a pumping system which can position the buffer fluid over the gel and replace the buffer fluid as needed. This facilitates use of the electrophoresis system of the preferred embodiment in that the operator does not have to manually position the buffer fluid over the gel and the electrophoresis process can be controlled, to some extent, by using a buffer fluid maintained at a uniform temperature.

Hence, the system of the present invention allows for automated capture of electrophoresis data over time, thereby reducing the inefficiencies associated with the operator manually capturing images of an electrophoresis sample and the like. The automated operation is facilitated by the automated determination of the locations within the samples that will contain the electrophoretic material.

The data obtained by the system of the preferred embodiment is also more accurate as each image is digitally processed to remove the background. Further, the data obtained by the system of the present invention can be further processed to give an indication of the quantity of molecules that are present within a particular well. Thus, the system of the present invention is more versatile and provides better data than prior art electrophoresis systems. These and other objects and advantages of the present invention will become more fully apparent from the following description taken in conjunction with the accompanying drawings.

DETAILED DESCRIPTION OF THE PREFERRED EMBODIMENT

Figure 1:
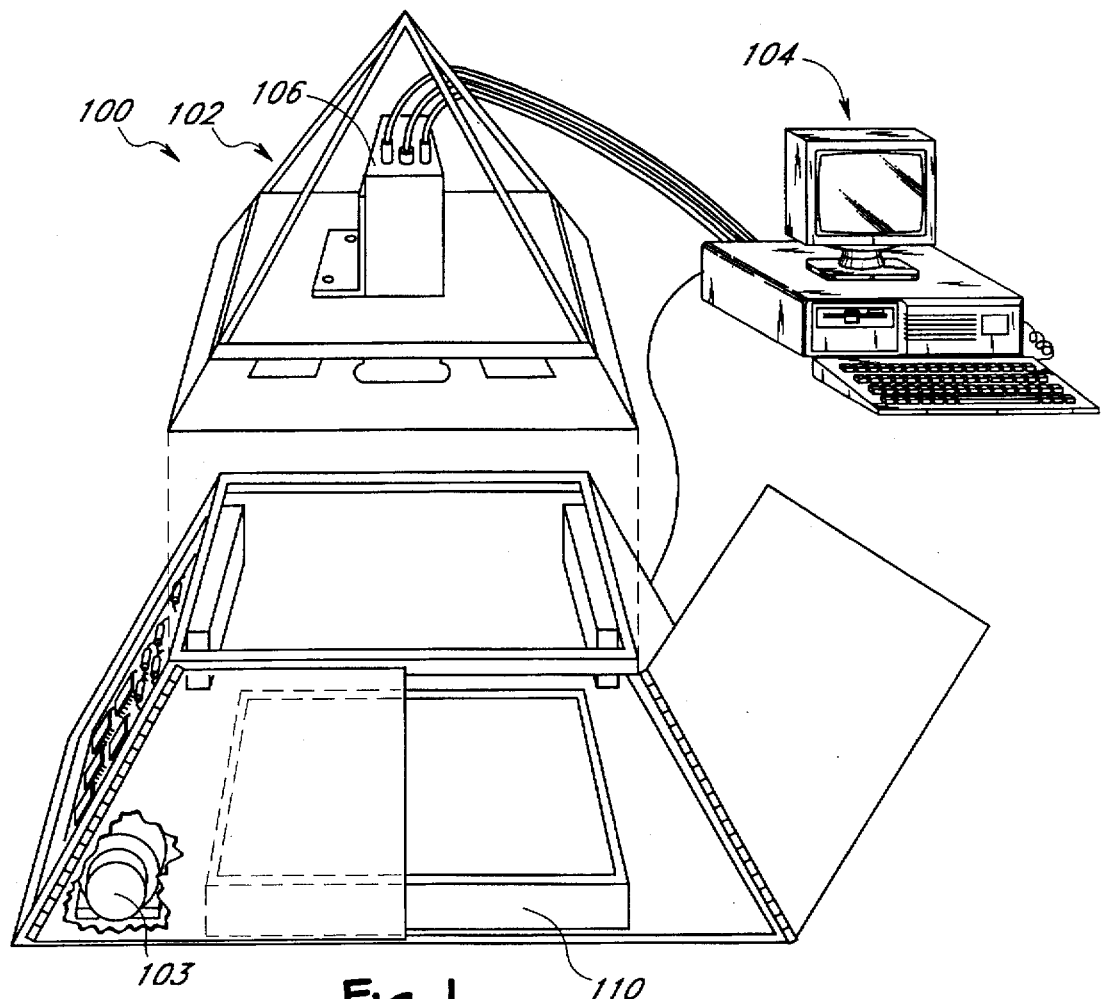
FIG. 1 is a perspective view of a preferred embodiment of an automated electrophoresis system of the present invention.
Figure 2:
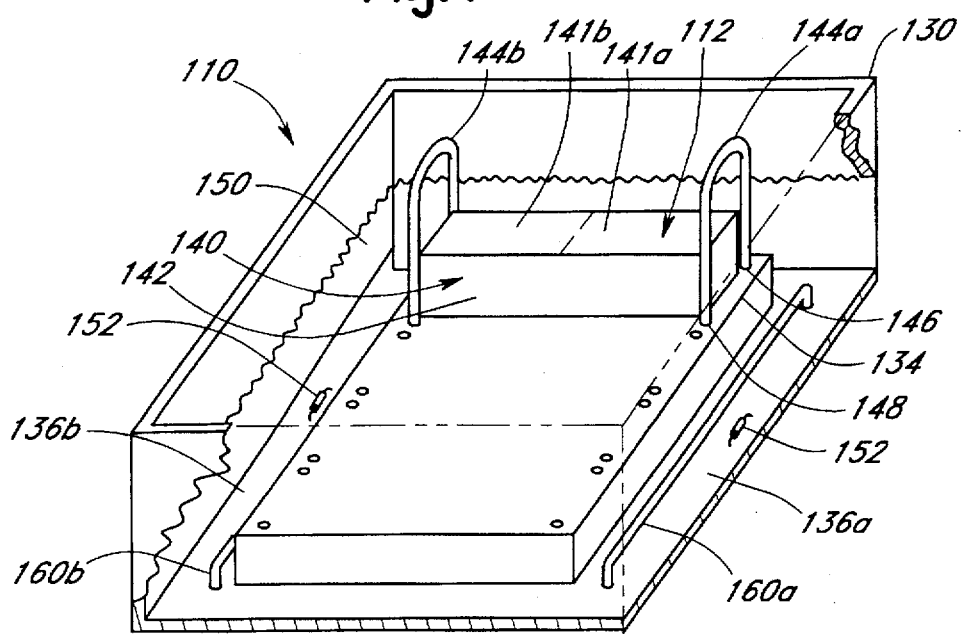
FIG. 2 is a perspective view of a sample platform of the automated electrophoresis system of FIG. 1.

Reference will now be made to the drawings wherein like numerals refer to like parts throughout. FIGS. 1 and 2 illustrate the automated electrophoresis system 100 of the preferred embodiment. In particular, the system 100 includes an enclosure 102, a personal computer 104 and a buffer pump and heating system 103. Within the enclosure 102, there is an image capture device 106, which in the preferred embodiment is preferably a CCD camera and an electrophoresis platform 110 wherein one or more electrophoresis samples 112 will be positioned. Further, one or more ultraviolet lights 114 (FIG. 2) are also mounted within the enclosure 102 so as to illuminate electrophoresis sample 112. In addition, a voltage supply 105 (FIG. 3) is positioned within the enclosure 102 so as to provide a voltage to the sample to induce electrophoresis migration.

As shown in FIG. 1, the enclosure 102 of the preferred embodiment preferably is in the configuration of a pyramid. This allows the image capture device 106 to be mounted above the platform 110 and the electronics (not shown) contained within the enclosure 102 to be mounted on the base of the enclosure 102. The enclosure 102 also includes two doors 111a and 111b that allow the operator access to the platform 112 so that samples 112 can be positioned within the enclosure in the manner that is described in greater detail in reference to FIG. 2.

Preferably, the electrophoresis samples 112 are positioned on the electrophoresis platform 110 within the enclosure 102. The platform and samples are described in greater detail hereinbelow in reference to FIG. 2. The computer 104 induces the buffer pump 103 to supply buffer fluid having a desired temperature to the samples 112 so as to submerge the samples in the buffer fluid. Preferably, there is a sensor on the platform that determines when the level of buffer fluid has dropped below a desired amount so as to signal the computer 104 to induce the pump system 103 to add additional buffer fluid. Periodically, the computer 104 induces the pump system 103 to drain out excess buffer fluid to a waste buffer vessel (not shown). The computer 104 thereby controls the buffer system so as to minimize waste of the buffer material and to automatically replace buffer material while maintaining the buffer fluid at a desired temperature.

The personal computer 104 also causes a voltage to be applied to the electrophoresis sample 112 after the buffer fluid is loaded which initiates the electrophoresis process. During the process, the image capture system 106 periodically captures an image of the electrophoresis sample 112 and provides this image to the personal computer 104. The exact operation of the system 100 will be described in greater detail in reference to the flow chart shown in FIGS. 4–6 hereinbelow.

A preferred embodiment of the sample platform 110 is shown in greater detail in FIG. 2. Specifically, the sample platform 110 includes an enclosure 130 that has an opening 132 on an upper surface and a platform 134 extending substantially the full length of the enclosure 130 so as to define two wells 136a and 136b. A sample 112 is positioned within a sample cradle 140 and the sample cradle 140 is then positioned on the platform 134. As shown in FIG. 2, the sample cradle 140 is comprised of a bed portion 142 that holds the sample gel 112 and two holders 144a and 144b positioned at the longitudinal ends of the bed portion 142.

Preferably, the holders 144a and 144b have posts 146 that extend downward and holes 148 are formed in the platform 134 that are configured to receive the posts 146.

The operator simply has to position the gel material 112 into the sample cradle 140 and then use a comb to form starting wells within the sample gel. In the preferred embodiment, each of the sample gels 112 can have up to 10 starting wells formed therein. Molecular material is then positioned in one or more of the starting wells and the sample cradle 140 is then positioned on the platform 134. The sample cradles 140 with the handles 144a, 144b is configured so that the operator can position the cradle on the platform 134 by grasping the handles and then lowering the cradle 140 into the desired position. In the preferred embodiment, the operator can position the cradles 140 into the enclosure at any time and then start the electrophoresis process on the sample material contained within the starting wells of the cradle.

A quantity of buffer solution 150 is provided from the buffer pump 103 (FIG. 1) via an apertures 152 into the wells 136a and 136b. Preferably, there is a sufficient quantity of buffer solution 150 to fully cover the sample gels 112 positioned within the sample cradles 140 that are positioned on the platform 134. The buffer solution 150 is preferably an ionic solution that is maintained at a desired temperature by a heater associated with the pump 103. In the preferred embodiment, the apertures 152 are controllable so that the solution can be periodically replaced or refreshed. FIG. 2 also illustrates that there are two electrodes 160 that extend lengthwise along the wells 136a and 136b.

The two electrodes 160a and 160b provides the electrical stimulus to induce electrophoretic migration of the samples positioned within the starting wells. Specifically, the buffer solution 150 is an ionic based solution so that application of an electrical signal to the electrodes 160a and 160b results in the electrical signal being transmitted in the solution between the electrodes. This produces an electric field that extends in a direction that is parallel to the length of the sample gels 112. The sample material positioned in the starting wells migrates in a direction that is parallel to the length of the sample gels 112 in response to the applied electric field.

As shown in FIG. 2, the platform 134 is configured to hold up to four sample cradles each of which contains sample gels 112 that can accommodate up to ten different starting wells within each half 141 of the sample gel that will receive the sample material that is to be tested by electrophoresis. Consequently, the electrophoresis apparatus of the preferred embodiment is capable of performing an electrophoresis run on up to eighty different samples at any one time. It will be further appreciated from the following description, that the automated system of the preferred embodiment is also automatically capable of determining where electrophoresis samples have been position on the platform and then registering information about these samples in these locations as the electrophoresis process continues.

Figure 3:
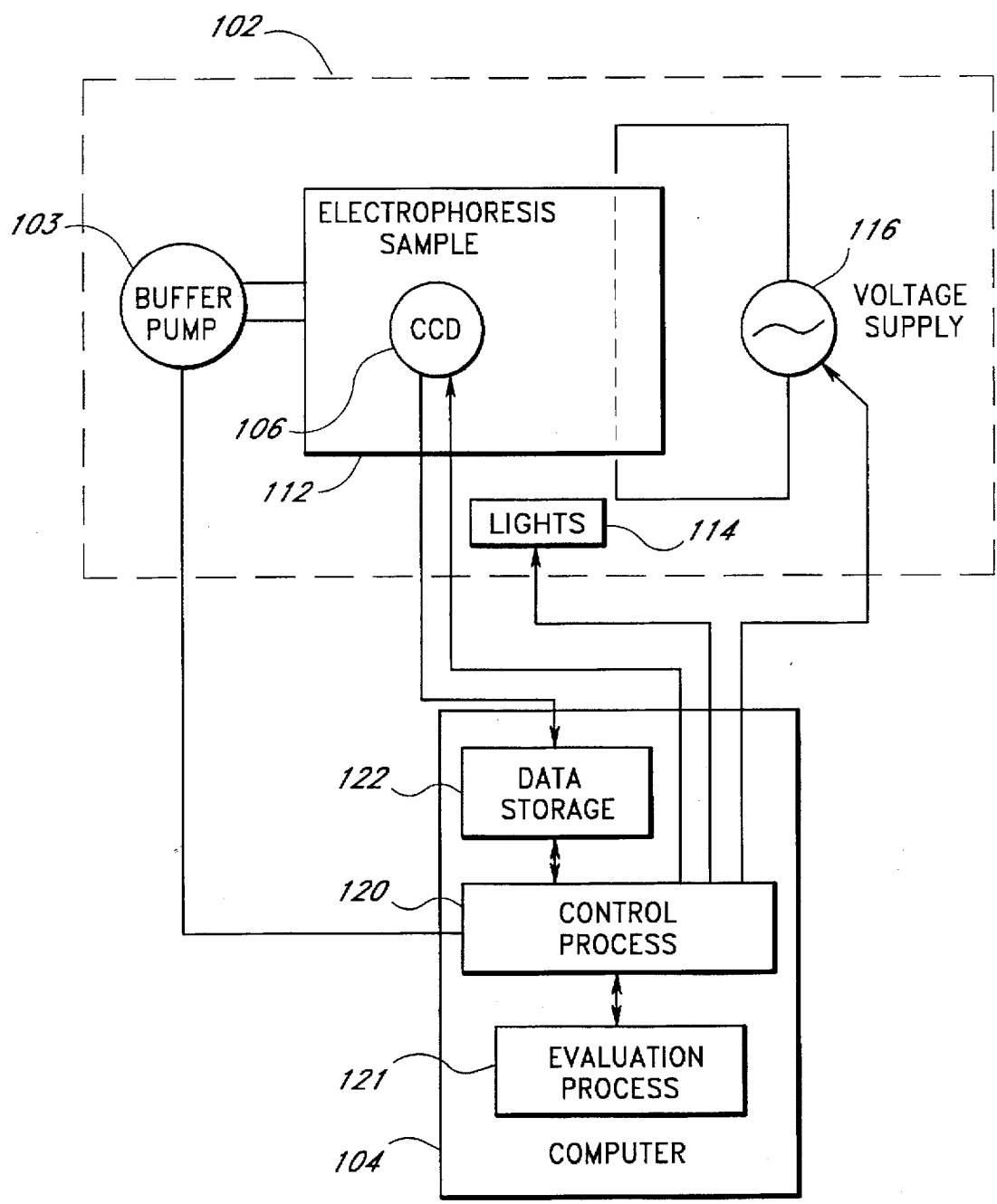
FIG. 3 is a schematic illustrating the components of the automated electrophoresis system of FIG. 1.

FIG. 3 is a schematic drawing which illustrates the functional relationship between the components of the automated electrophoresis system 100 in greater detail. Specifically, the electrophoresis sample 112 is positioned within the enclosure 102. A voltage is applied to the samples 112 from a voltage supply 116 via the electrodes. This induces the molecules that are deposited into a plurality of starting wells in the sample 112 to migrate through the sample. As is understood in the art, the presence or absence of the molecules at different positions in the sample is indicative of the presence or absence of particular molecules within the sample being tested by electrophoresis. The system 100 periodically fluoresces the sample 112 with the ultraviolet lights 114 and then captures an image of the sample 112 using the image capture system 106.

As is shown in FIG. 3, the personal computer 104 is logically organized to include a control process 120 which provides control signals to the voltage supply 116, the lights 114, the buffer system 103 and the camera 106 so as to automatically initiate the electrophoresis process and then periodically capture electrophoresis data from the sample 112 in the manner that will be described in greater detail in reference to FIGS. 4-6 hereinbelow. Further, the personal computer 104 also includes an evaluation process 121 that performs evaluation of the data obtained by the control process 120 and a data storage structure 122 wherein data from the image capture system is stored within the computer 104. During the electrophoresis process, the control process 120 can induce the buffer system 103 to periodically drain and replace the buffer solution in the platform at periodic intervals.

Figure 4:
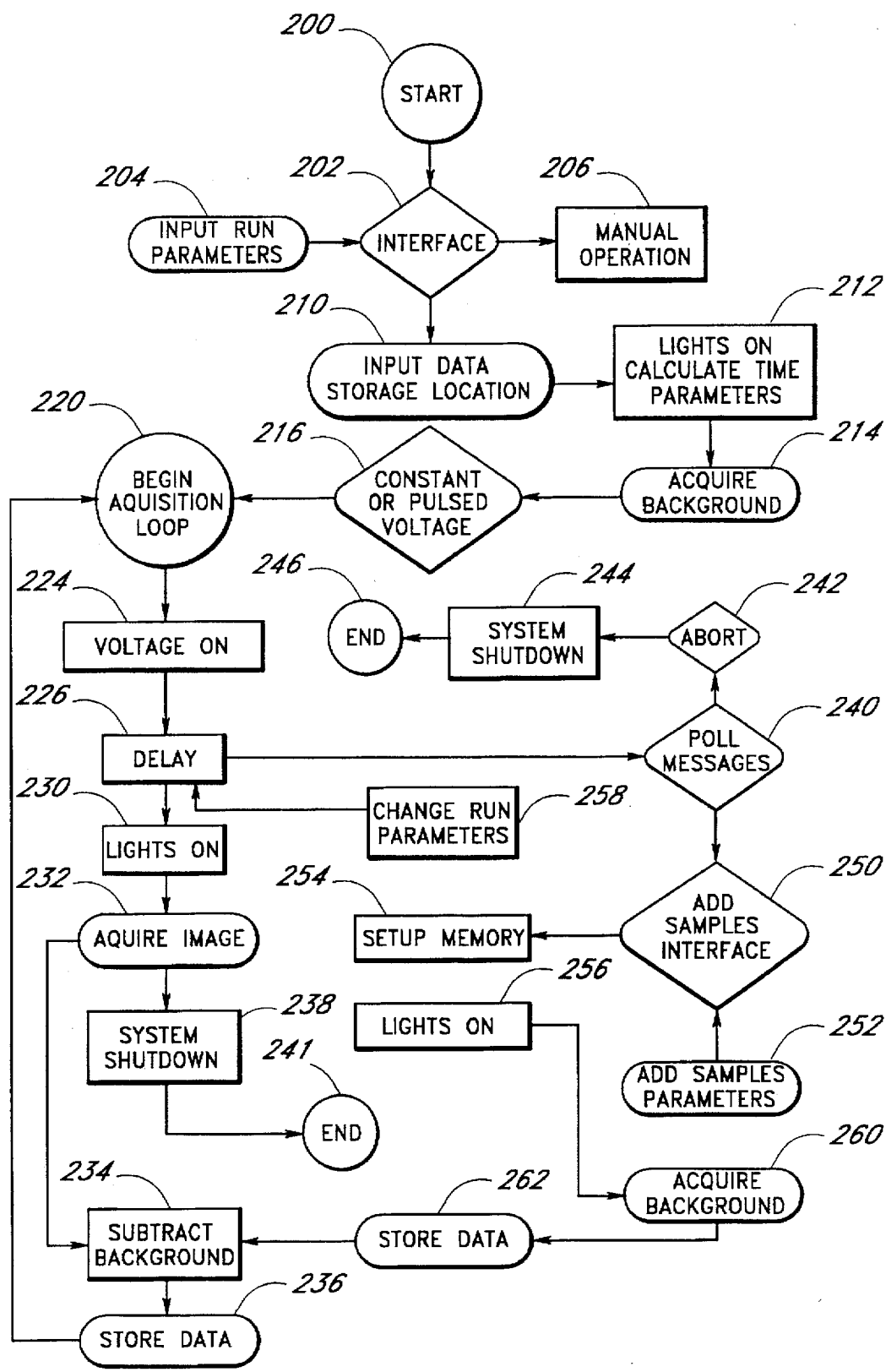
FIG. 4 is a flow chart which illustrates a data acquisition process performed by the automated electrophoresis system shown in FIG. 1.
Figure 5:
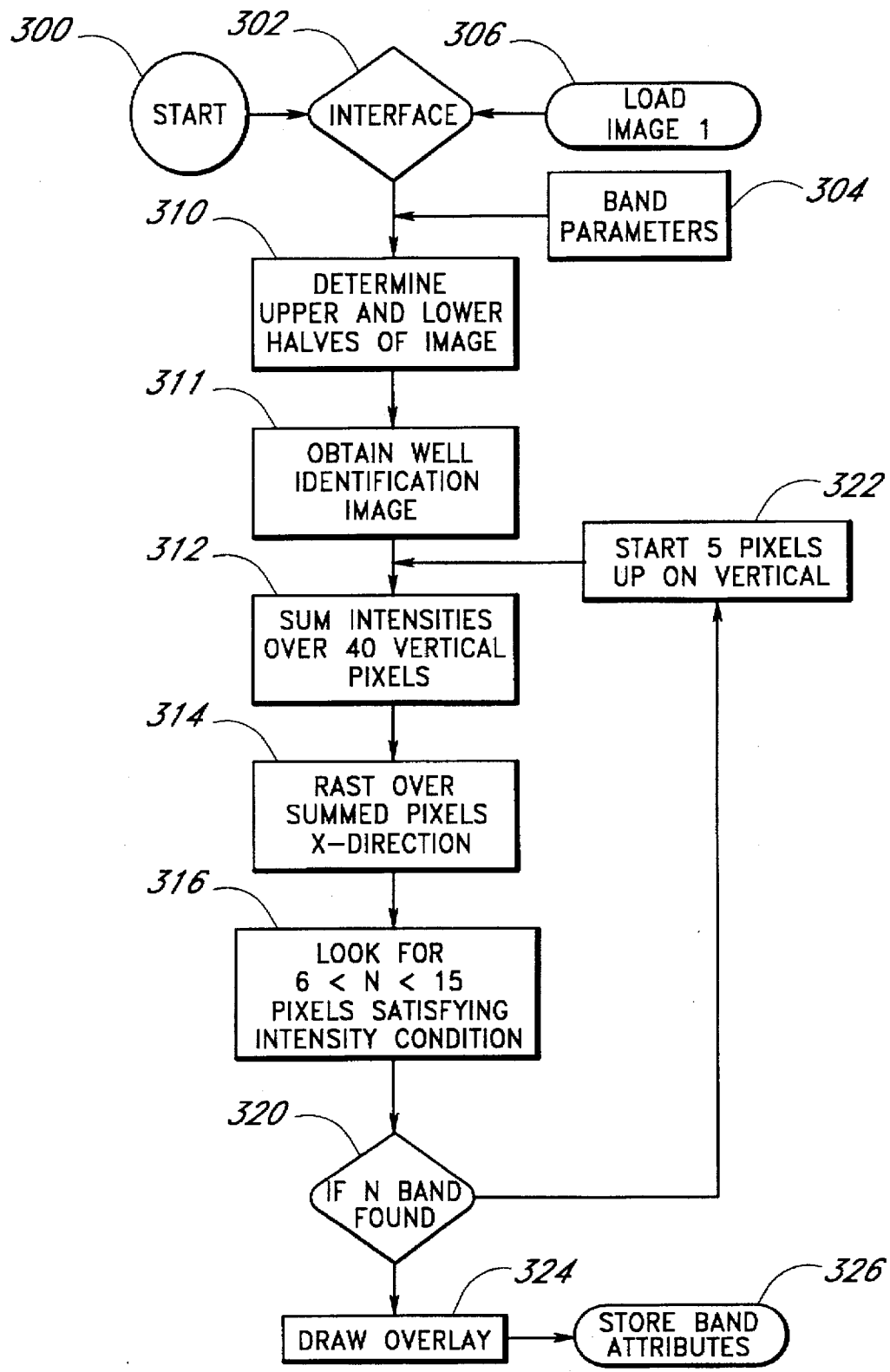
FIG. 5 is a flow chart which illustrates a process whereby the positions of the occupied wells on a sample are determined by the automated electrophoresis system of FIG. 1.
Figure 6:
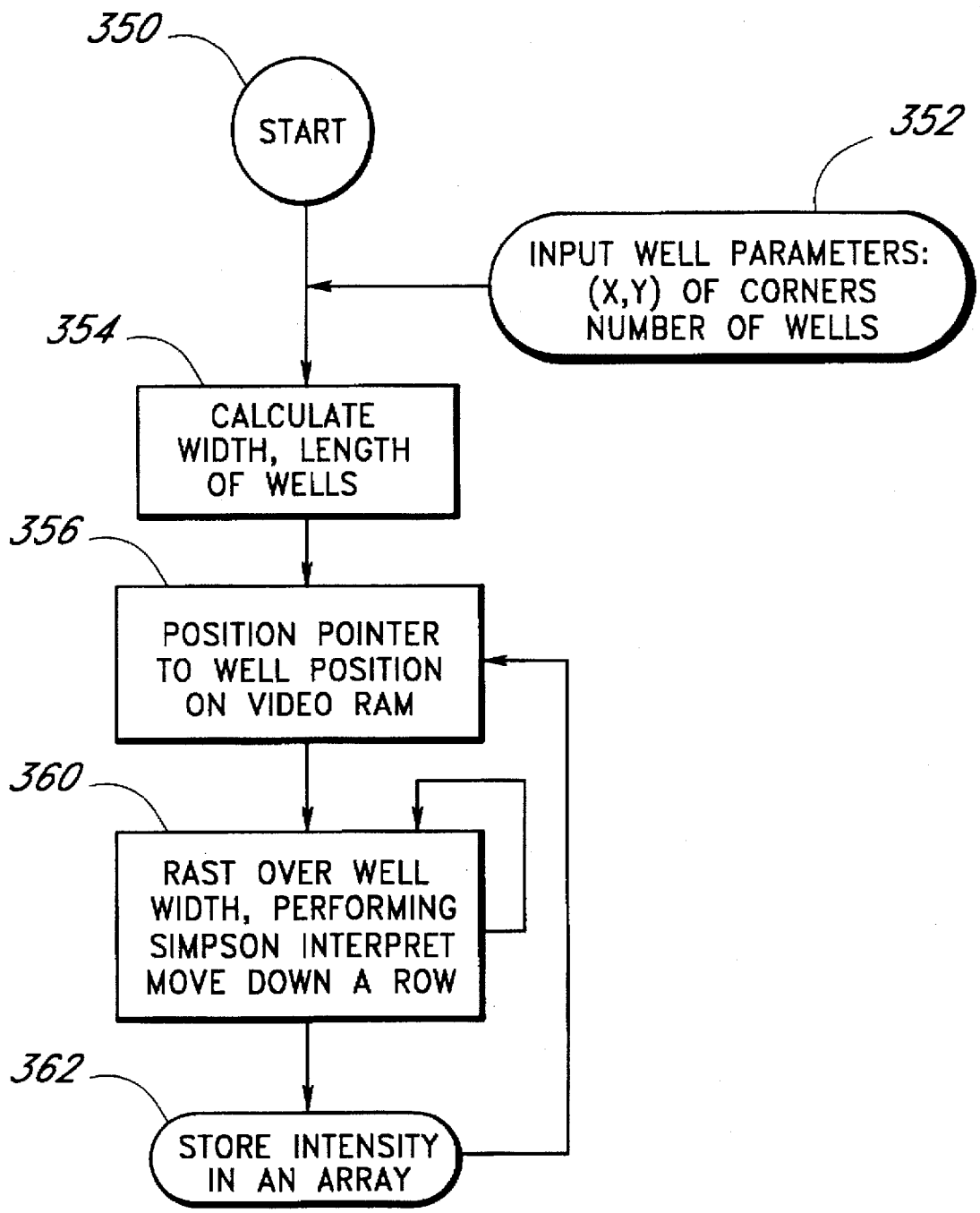
FIG. 6 is a flow chart which illustrates the process by which the automated electrophoresis system of FIG. 1 determines the intensity of the wells.

It should be appreciated that the organization of the computer 104 and the control process 120 and the sequence of operation described by the flow charts of FIGS. 4-6 are simply exemplary of one preferred method of implementing the system of the present invention. In the preferred embodiment, the computer 104 is an IBM compatible computer and the computer programs illustrated in FIGS. 4-6 are implemented using a Windows™ based operating system.

Referring now to FIG. 4, the operation of the computer 102 and, in particular, the operation control process 120, while the electrophoresis system 100 acquires data, will be described. Initially, from a start state 200 the control process 120 enters an interface decision block 202 wherein the operator will have the option of either entering a manual operation function 206 wherein the electrophoresis will be controlled manually or, in a function 204, inputing the automated run parameters. In particular, the run parameters for automated operation of the system 100 would include the run time, which is the length of time that the system 100 will allow the electrophoresis process to continue, the voltage signal that is to be applied to the electrophoresis samples 112 by the voltage supply 116, the gel size, which is indicative of the width of the gel in the electrophoresis sample 112, and an integration parameter which controls the speed of the shutter of the CCD camera 106.

Once the run parameters have been input in function 204, the control process 120 then prompts, in a state 210, the operator to designate the file in which the data acquired during the subsequent computer run is going to be stored, i.e., the data storage location within the data storage block 122 (FIG. 3). Once the data storage location has been designated in state 210, the control process 120, in state 212, turns the lights on and then determines when, and how long, the lights will be turned on during each of the time periods where images of the sample are to be captured.

Subsequently, the control process 120 then enters a function 214 wherein it acquires a background image of the sample 112. In the preferred embodiment of the system 100, one or more submarine slab gels are positioned within the enclosure 102 and a comb is inserted into the slab gels to form a series of starting wells that are spaced apart in a fixed orientation. The sample material is then positioned in the starting wells which are preferably located adjacent one edge of the sample gels 112 (FIG. 2). An example of the electrophoresis process will be described in reference to the diagrams of FIG. 7 hereinbelow.

By taking the background picture 214 prior to the beginning of the electrophoresis process, the system 100 can establish a baseline image of the slab gels and can use this baseline image in comparison with subsequently taken images to acquire data indicative of the movement of the molecules to be tested in electrophoresis as a result of the applied voltage. In the preferred embodiment, the background image is acquired in state 214 by a CCD device taking an image of the slab gel sample as it is positioned within the enclosure 102 and then storing this image in a location in the appropriate data storage structure 122 of the computer 104.

Subsequent to acquiring the background image, the control process 120 then ascertains, in decision state 216, whether the voltage that is to be applied to the electrophoresis sample 112 is either a constant or pulsed voltage. As explained in reference to state 204, the operator in the preferred embodiment has the ability to select the voltage characteristic. It will be further appreciated that the exact configuration of the voltage that is applied to the electrophoresis sample will vary depending upon the application.

The control process 120 then begins an acquisition loop in a state 220 wherein images of the sample 112 will be taken at discrete time intervals and the images will then be stored in the data storage unit 122 of the computer 104. The acquisition loop 220 initially begins with the control process 120 instructing the voltage source 116 to turn on in a state 224. Once the voltage source is on in state 224, the control process then enters a delay state 226 wherein the electrophoresis process is occurring in the sample 112. Specifically, the molecules of matter that have been deposited into the series of starting wells are beginning to migrate through the gel in response to the applied voltage. During the delay state 226, the control process 120 polls for messages in a state 240 in a manner that will be described below.

After the delay period, the control process 120 then initiates a sequence wherein an image of the sample is to be acquired and data relating to the sample is then stored in the memory of the computer 104. Specifically, in a state 230 the control process 120 instructs the ultraviolet lights 114 to turn on. This illuminates the florescent molecules that are mixed with the sample material. As is generally understood in this art, the fluorescent molecules are attracted to sample molecules during the electrophoresis process in proportion to the quantity of sample molecules present. Hence, any subsequent image of the samples will include fluorescent bands the intensity of which are in proportion to the quantity of sample material in the band. Consequently, by turning the lights on in state 230, the molecules that have migrated from the starting wells will be illuminated. While the molecules are fluorescing, the control process 120 instructs the image acquisition device 106 to acquire an image of the sample 112. The image is then stored and the control process 120, in a state 234, digitally subtracts, in state 234, the background acquired in state 214 from the image acquired in state 232. As discussed above, the CCD camera obtains a digital image of the sample gels positioned on the platform 110. This digital image is comprised of a plurality of pixels having an assigned intensity value. Preferably, the intensity values of the background image is subtracted form the intensity values of the subsequently taken image to obtain a final image of the sample gels that is background adjusted.

Consequently, the control process 120 obtains a digital image that is indicative of the change in the sample gels during the electrophoresis process. Subsequent to the digital subtraction, the control process 120 then stores the data, in state 236, in the data storage location designated in state 210. The control process 120 repeats the loop comprised of the states 220 through 236 until the loop has been completed a preselected number of times. Once the loop has been completed the preselected number of times, the control process 120 then enters a shutdown state 238 from which the process then proceeds to an end state 242. Further, the control process 120 in the preferred embodiment also records in a log file in the data structure 122 data indicative of the performed process. Hence, the control process 120 can thereby build a global log file and a temporary log file that contains information indicative of the samples processed by the system 100.

It will be appreciated that the system 100 allows the user to prepare the sample, position the sample within the enclosure, designate the time period of the electrophoresis process and the applied voltage and the system then automatically performs the electrophoresis process and periodically obtains data during the process time. Further, as described above, the system 100 also automatically fills the sample with an appropriate buffer material, when needed. The delay in the delay state 226 is, of course, dependent upon the number of times the operator has instructed the system 100 to obtain images and the length of time the operator has instructed the system 100 to perform the electrophoresis process.

Further, during the delay time 226, the control process 120 polls for messages in a decision state 240. Basically, the control process 120 looks for other commands emanating from the personal computer 104 during the delay period 226. If the control process 120 determines in decision state 240 that the control process 120 has been instructed to enter an abort state 242, the control process 120 enters the abort state and ends the electrophoresis process by turning off the power supply, the lights, etc.

Further, as illustrated in FIG. 2, in the preferred embodiment, the electrophoresis platform 110 is large enough to accommodate multiple samples 112. It may be that the operator may decide to position a new sample within the enclosure 102 while the previous samples are being subjected to the electrophoresis process. The operator simply has to instruct the control process 120 via a keyboard or a mouse of the computer 104 that it wishes to add additional samples to cause the control process 120 to enter a state 250 wherein additional samples will be added. Subsequently, the operator, in state 252, adds the sample parameters that control the electrophoresis process for the new sample. The parameters entered in state 252 are similar to the parameters that the operator had entered in state 204 for the original samples. Subsequently, the control process 120 sets up the data storage unit 122 to store images corresponding to the new samples in state 254 and change the original run parameters in state 258 and initiate the process. At this time, if buffer fluid is needed for the new sample, the control process 120 instructs the buffer system 103 to add buffer fluid to the sample.

The control process 120 then initiates a background capture function 260 for the newly added sample 112. Specifically, the control process 120 induces the florescent lights 114 to turn on in state 256 and also induces the image acquisition device 106 to acquire a background shot in state 260 for the new sample 112. This background shot is then stored in state 262 in the data storage section 122 of the computer 104 in the previously described manner. Subsequently, the electrophoresis loop 220 is then allowed to continue for all of the samples that are within the enclosure 104 including the newly added sample. Hence, the system of the preferred embodiment allows the operator to easily add new and additional samples to the electrophoresis enclosure while other samples are being processed.

The description provided in conjunction with FIG. 3 describes the manner in which data is automatically obtained during the electrophoresis run. It will be appreciated that the storage unit section 122 of the computer 104 will have digital data representative of the image of the samples 112 at discrete time intervals during the electrophoresis process. These images can be displayed on the display of the personal computer at the command of the operator. Further, the system will also allow the operator to form calculations and determine locations of each of the bands of sample molecules from the images that have been acquired in the loop 220. The data acquisition and calculations will be described in reference to FIGS. 5 and 6 hereinbelow.

FIG. 5 is a flow chart which illustrates the function performed by the evaluation process 121 to determine the locations of occupied starting wells within the sample image 112. It will be appreciated that the evaluation process 121 stored in the storage structure 122 a plurality of refined digital images of the sample 112. In particular, the stored digital images are digital image of the samples 112 after the background image has been subtracted from the subsequently taken image.

The evaluation process 121 in this function then automatically determines the locations of the occupied starting wells in the sample 112. Once the occupied starting wells have been identified, the portion or region of the sample gel 112 that contains the sample material can then be defined. This simplifies the location and intensity analysis of the subsequently obtained images.

Specifically, the evaluation process 121 enters an interface function 302 wherein the user will be able to enter some band parameters in a function 304. In particular, the band parameters entered in function 304 include the number of bands and the widths of the bands, i.e., the number of pixels along the horizontal axis, that the evaluation process 121 will search for during the well acquisition function.

The evaluation process then enters a function 306 wherein the user can instruct the evaluation process 121, in state 306, to load particular images that have been captured during the automated run time program described above. The evaluation process 121 then determines which half of the image is being evaluated. In the preferred embodiment, the sample gel can be configured to be a single gel extending the full width of the platform 134 (FIG. 2) or the gel can be divided into the two sections 141a and 141b with the top of each section containing starting wells with sample material positioned therein. The operator preferably provides a signal to the computer 104 as to whether the cradles have been divided into two sections positioned across the width of the pedestal 110. This information instructs the evaluation process 121 as to where to look to find the position of the occupied starting wells.

Figure 7A:
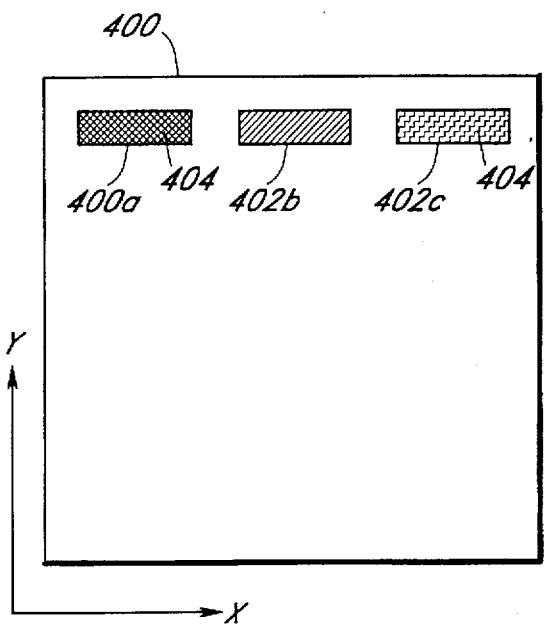
FIGS. 7A–7D are schematic illustrations of exemplary images of sample gels containing sample material that are used to determined the location of occupied starting wells in the sample gel.
Figure 7C:
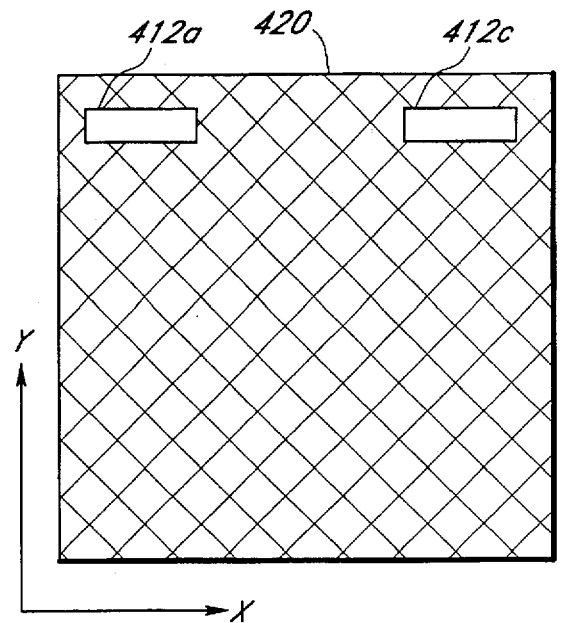
Figure 7B:
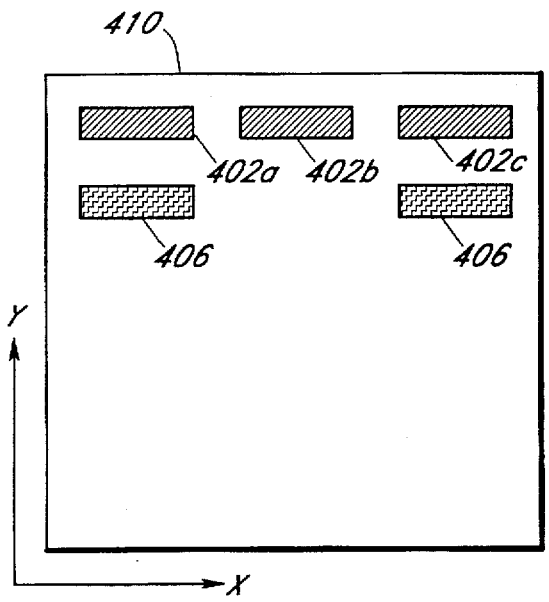

Subsequently, the evaluation process 121 then processes the first image in state 311 to obtain a well identification image. For clarity, the description of the starting well location process will also be explained in reference to the simplified exemplary diagrams of FIG. 7. FIG. 7A exemplifies a typical background image 400 with three starting wells 402a, 402b and 402c wherein two of the outer wells 402a and 402c have been loaded with sample material 404. FIG. 7B exemplifies a typical first image that has been taken approximately 5 minutes after the initiation of the electrophoresis process.

In the preferred embodiment, in the first image 410 (shown in FIG. 7B) a loading buffer 406 that is included in the sample material 404 migrates out of the starting wells 402a and 402c. The subtraction of the background image 400 from the first image 410 results in an image 420 where the occupied starting wells 402a and 402c appears as a light spot 412a and 412c on a dark background due to the migration of the loading buffer 406. Subsequently, the image 420 is then negated, so that in the resulting image 430 the occupied starting wells 402a and 402c appears as a black band 440a and 440b on a white screen where the black bands 440 corresponds to the position of the occupied starting wells 402a and 402c. It will be appreciated in reference to FIG. 7D that if no loading buffer was positioned within a starting well, the resulting image will not produce a black band in the position of the unloaded starting well.

Figure 7D:
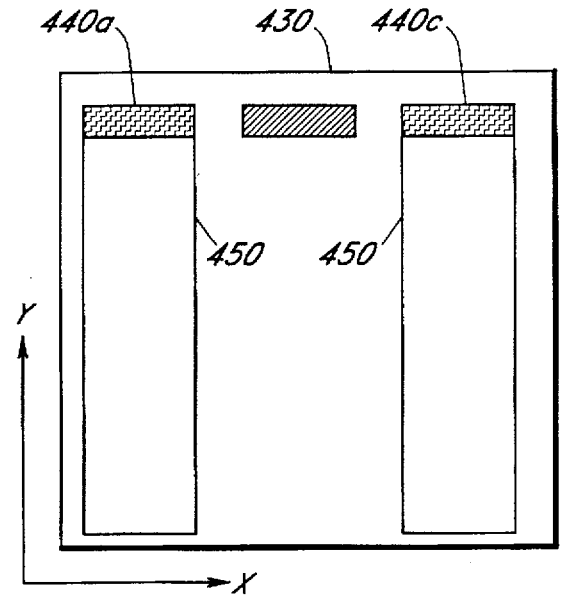

The evaluation process 121 then enters a loop, comprising the states 312–322, wherein intensity values of the pixels are summed and analyzed to determine the location of high intensity bands in the image of FIG. 7D corresponding to occupied starting wells in the sample 112. In particular, the evaluation process in state 312 initially sums the intensities of 40 vertical pixels (y direction) of the image provided in state 306. Once the intensities of 40 vertical pixels have been summed, the evaluation process then, in a state 314, initiates a function 314 whereby the evaluation process rasts over the summed pixels in the horizontal or x direction across the full width of the image of FIG. 7D. During the function 314, the evaluation process is searching, in state 316, for pixels that satisfy an intensity condition and size condition which is indicative of the presence of a high intensity band corresponding to an occupied starting well in the sample 112.

The evaluation process then determines, in decision state 320, if a band corresponding to a starting well has been found has been found. If no band has been found, the evaluation process 121 then jumps five vertical pixels up, in state 322, and then initiates the loop comprising the states 312–320 again. Hence, the evaluation process 121 vertically sums the pixels and then horizontally scans the summed pixels looking for the highest intensity values of summed pixels to determine the location of starting wells.

Once the evaluation process determines in state 320 that a starting well has been found, it then enters a define well parameters/draw overlay function 324 wherein an overlay 450a and 450b (FIG. 7D) is produced for each identified occupied starting well 402a, 402c. The overlay 450a and 450b has approximately the same width in the X direction as the occupied starting well and extends the full length of the sample gel 112. The overlays 450a and 450b correspond to the area on the sample 112 that the sample material 404 is going to migrate within the sample 112 during the electrophoretic migration. Hence, the configuration of the overlays 450a and 450b is dependent upon the applied electric field and defines the region of pixels on the subsequent images taken of the sample that the evaluation process 121 should look to determine locations and intensities of florescent bands. Subsequently, the evaluation process 121 then stores the well's attributes, e.g., its location and width, in state 326. This allows the evaluation process 121 to identify the locations of the starting wells in the sample and identify a column or region of the sample 112 associated with the well where corresponding bands of migrating bio-molecules will occur as subsequent images. This information can then be used to determine the presence or absence of particular molecules being tested within the electrophoresis sample.

FIG. 6 is a flow chart which illustrates the function performed by the evaluation process 122 to obtain a location and an integrated intensity value corresponding to each of the starting wells located in the automated well acquisition function described in reference to FIG. 5. For clarity, the operation of the evaluation process 121 while performing this function will also be described in reference to the flowchart of FIG. 6 and the exemplary sample image of FIG. 8.

Specifically, from a start state 350, the evaluation process 121 enters a function 352 wherein the well parameters are recalled. The coordinate locations of the overlays 450a and 450b and their coordinate locations determined in the function described above is downloaded from the data structure 122. The width generally corresponds to the width of the starting well and the column corresponds to the vertical column of pixels extending from the starting well to the edge of the sample 112.

Figure 8:
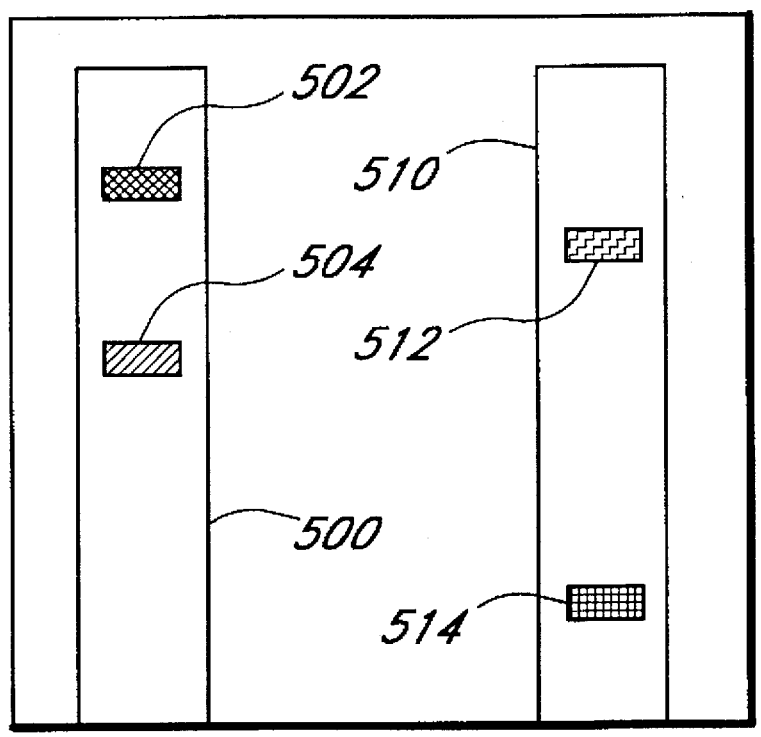
FIG. 8 is a schematic illustration of an exemplary image of a sample gel after application of the electrophoresis process wherein the sample material has migrated through the gel to locations within one or more pre-defined wells.

In the preferred embodiment, the image that is being evaluated is preferably displayed on a display (FIG. 1) of the personal computer 104 in the manner shown in FIG. 8. Specifically, the recalled image will have dark bands positioned within the designated overlays 450a, 450b wherein the dark bands correspond to the florescent bands that are received by the image capture device when the digital images of the sample are obtained in the manner described above. In general, the evaluation process 121 performs a function whereby the location and integrated intensity of the bands is determined for each of the occupied starting wells in the sample. Alternatively, the operator can then select the column and well in state 356 wherein the location and integrated intensity is to be determined by using a mouse to position a cursor on the well and column. The evaluation process 121 then, in state 360, rasts over each of the rows of the pixels (x-direction) within the selected column or well and performs a Simpson integration of the intensity values for each of the pixels in the row. This process is repeated for each of the rows within the selected column and the integrated intensity values are stored in an array in state 362. It will be appreciated that the processing of the computer 104 to determine the integrated intensities is simplified by the defining of the well attributes which results in the development of the overlays in that the data for only the pixels contained within the defined wells must be evaluated. It will further be appreciated that, instead of the computer determining the location and integrated intensities of the selected columns, that the computer 104 can be instructed to automatically determine the location and integrated intensity information for each of the columns in the sample and then store the data for further evaluation within the automated run sequence.

Hence, there is an intensity value for each row in the column stored in an array. The integrated intensity values for each of the rows are indicative of the presence or absence of bands within a row. Consequently, referring to FIG. 8, there will be an array of integrated intensity values that correspond to the well 500. This data will include intensity values that identify the location of a first fluorescing band 502 of a first intensity in the well 500 and a second fluorescing band 504 in the well 500. Similarly, an array of data can also be assembled for the well 510 for the bands 512 and 514. Since there is an array of integrated intensity values for each row, the intensity values will rise when a band is detected. For example, the integrated intensity values may have a Gaussian distribution at or near the location of a band. This information can then be used to determine the position of bands of bio-molecules within the sample. Further, the integrated intensity value does provide information as to the quantity of molecules found within a portion of the sample.

This process can be repeated, using the system 100 for each of the starting wells in each of the stored images of the sample. Both the band location and the quantity information can then be used for many different types of comparative electrophoresis analysis. Hence, the system of the preferred embodiment automatically induces an electrophoresis process on a sample, automatically acquires the data. The data can then be analyzed to determine the locations and the wells containing bio-molecules following the electrophoresis process and can also be used to obtain data that is indicative of the quantity of molecules within particular regions of the sample gel.

Although the foregoing description of the preferred embodiment of the present invention has shown, described, and pointed out the fundamental novel features of the invention, it will be understood that various omissions, substitutions, and changes in the form of the detail of the apparatus as illustrated, as well as the uses thereof, may be made by those skilled in the art, without departing from the spirit of the present invention.

What is claimed is:

1. A system for obtaining electrophoresis data comprising:
   a platform configured to hold one or more electrophoresis samples wherein sample material can be positioned in one or more starting wells in the one or more samples;
   a voltage supply capable of inducing electrophoretic migration of the sample material contained within the one or more starting wells;
   an image capture device which captures images of the one or more samples positioned on said platform;
   a control process which receives signals from the image capture device and provides signals to the voltage supply to initiate the electrophoresis process and to the image capture device to induce the image capture device to capture images of the one or more electrophoresis samples, wherein the controller induces the image capture device to obtain a background image of the one or more samples, then induces the power supply to induce electrophoretic migration of the sample material positioned within the one or more starting wells and then induce the image capture device to capture a first image of the one or more electrophoresis samples; and
   an evaluation process which receives signals from the control process that are representative of the images obtained by the image capture device, wherein the evaluation process automatically determines the locations of occupied starting wells in the one or more samples and then defines one or more regions corresponding to the one or more occupied starting wells where subsequent electrophoretic migration will occur.

2. The system of claim 1, wherein the sample is comprised of an Agar gel and fluorescent molecules and wherein the sample material is comprised of molecular material positioned within the one or more starting wells.

3. The system of claim 2, further comprising:
   an enclosure that contains the platform and the image capture device; and
   one or more florescent lights that illuminate the platform containing the sample, wherein the control process selectively inducing the one or more florescent lights to illuminate the sample prior to inducing the image capture device to capture an image of the one or more samples.

4. The system of claim 3, wherein the image capture device is a CCD camera that obtains digital images of the samples that are comprised of a plurality of pixels of varying intensities wherein the varying intensities correspond to the intensity of the sample material in a region of the sample gel.

5. The system of claim 4, wherein the evaluation process determines the regions of the one or more samples where subsequent electrophoretic migration will occur by creating an image wherein the position of the starting wells in the image can be determined.

6. The system of claim 5, wherein the image is created by digitally subtracting the intensity values of the background image from the first image on a pixel by pixel basis and then negating the subsequent image, wherein the positions of occupied starting wells in the resulting image appear as low intensity regions of the image.

7. The system of claim 6, wherein the regions are defined in the image by defining a column for each starting well wherein the width of the column is comprised of the width of the high intensity region corresponding to the starting well and the length is defined at a first end by the position of the starting well and extends in a direction that is substantially parallel to the direction of the electric field produced by the voltage supply.

8. The system of claim 7, wherein the control process obtains a plurality of images during the electrophoresis process and wherein the evaluation process evaluates the regions and obtains location and intensity data corresponding to bands of the sample material that has electrophoretically migrated in the one or more regions.

9. The system of claim 3, wherein the enclosure can receive multiple samples and wherein the control process is configured so that after inducing electrophoretic migration in a first sample, a second sample can be positioned within the enclosure and the control process can then be induced to obtain a background image and then continue the electrophoretic migration of the sample material in the first and second samples.

10. The system of claim 3, wherein the enclosure is in the shape of a pyramid having a base and an apex and wherein the image capture device is located at the apex of the pyramid and the platform is mounted within the base so as to be substantially centered under the apex.

11. A method of obtaining electrophoresis data comprising the steps of:
    positioning sample material within one or more starting wells in a sample gel;
    positioning the sample gel in an enclosure;
    applying an electrical signal to the sample gel so as to induce the sample material to electrophoretically migrate through the sample gel;
    periodically illuminating the sample gel;
    while illuminating the sample gel, periodically obtaining a digital image of the sample gel;
    defining a region of the sample gel wherein electrophoretic migration of the sample material will occur by identifying the location in a digital image where an occupied starting well is located and then defining a column for the digital image that has a width corresponding to the width of the occupied starting well and a length that extends from the position of the starting well in a direction that is substantially parallel to the direction of the electric field resulting from the applied voltage; and
    obtaining location data from a subsequently obtained digital image by superimposing the column on the subsequently obtained digital image and then recording the location of bands of migrated sample material within the column.

12. The method of claim 11, further comprising the steps of:
    obtaining a background image prior to applying the electrical signal; and
    subtracting the background image from the subsequently obtained images.

13. The method of claim 12, wherein the step of subtracting the background image comprises subtracting an intensity value for each pixel in the background image from the intensity value for each pixel in the subsequently obtained image.

14. The method of claim 11, wherein the step of periodically obtaining an image of the sample gel comprises using a CCD camera to obtain a digital image of the sample.

15. The method of claim 11, further comprising the step of obtaining intensity data of bands of migrated sample material within the column from a subsequently obtained digital image.

16. The method of claim 15, wherein the steps of obtaining location and intensity data comprises recording in an array digital data corresponding to the integrated intensity of each of a plurality of rows comprises the column wherein the integrated intensity data corresponds to the quantity of sample material that is positioned in a particular row of the column.

17. The method of claim 16, wherein the step of obtaining the integrated intensity data comprises performing a Simpson's integration over each of the pixels in each of the rows of the column.

* * * * *